US011103110B2

(12) United States Patent
Wall

(10) Patent No.: US 11,103,110 B2
(45) Date of Patent: Aug. 31, 2021

(54) FEMININE CLEANING DEVICE

(71) Applicant: Renae Wall, Irvine, CA (US)

(72) Inventor: Renae Wall, Irvine, CA (US)

( * ) Notice: Subject to any disclaimer, the term of this patent is extended or adjusted under 35 U.S.C. 154(b) by 754 days.

(21) Appl. No.: 15/777,889

(22) PCT Filed: Apr. 16, 2018

(86) PCT No.: PCT/US2018/027733
§ 371 (c)(1),
(2) Date: May 21, 2018

(87) PCT Pub. No.: WO2018/191742
PCT Pub. Date: Oct. 18, 2018

(65) Prior Publication Data

US 2021/0169280 A1 Jun. 10, 2021

Related U.S. Application Data

(60) Provisional application No. 62/485,783, filed on Apr. 14, 2017.

(51) Int. Cl.
*A61M 35/00* (2006.01)
*A47K 7/00* (2006.01)
(Continued)

(52) U.S. Cl.
CPC ................ *A47K 7/028* (2013.01); *A46B 1/00* (2013.01); *A46B 5/0029* (2013.01);
(Continued)

(58) Field of Classification Search
CPC .......... A47K 7/00; A47K 7/028; A61H 19/44; A61M 35/00; A46B 5/0029; A46B 1/00; A46B 5/0037; A46B 5/0095; A46B 9/005
See application file for complete search history.

(56) References Cited

U.S. PATENT DOCUMENTS 2,170,222 A * 8/1939 Strauss .................. A61F 13/38
604/2
3,228,398 A 1/1966 Leonard et al.
(Continued)

FOREIGN PATENT DOCUMENTS

| | | |
|---|---|---|
| CA | 2585826 A1 | 9/2008 |
| EP | 1034721 | 9/2000 |
| WO | WO 2012/022995 | 2/2012 |

OTHER PUBLICATIONS

International Search Report dated Oct. 29, 2018 in corresponding International Application No. PCT/US2018/027733 filed Apr. 16, 2018; total 3 pages.

(Continued)

*Primary Examiner* — Shay Karls
(74) *Attorney, Agent, or Firm* — Snell & Wilmer LLP

(57) ABSTRACT

A feminine cleaning device or brush for adult women for cleaning their vagina. The feminine cleaning brush includes a handle, a cleaning portion having rings arranged substantially parallel to one another and a groove positioned between adjacent rings. The number of rings being at least 10 and the number of grooves being at least 10. The feminine cleaning brush includes a middle portion positioned between the handle and the cleaning portion and a tapered tip extending from the cleaning portion. The tapered tip is provided for an easier and smoother insertion into the vagina.

17 Claims, 6 Drawing Sheets

(51) Int. Cl.

| | |
|---|---|
| ***A47K 7/02*** | (2006.01) |
| ***A46B 1/00*** | (2006.01) |
| ***A46B 5/00*** | (2006.01) |
| ***A46B 9/00*** | (2006.01) |
| *A61H 19/00* | (2006.01) |

(52) U.S. Cl.

CPC .......... *A46B 5/0037* (2013.01); *A46B 5/0095* (2013.01); *A46B 9/005* (2013.01); *A46B 2200/1006* (2013.01); *A61H 19/44* (2013.01)

(56) References Cited

U.S. PATENT DOCUMENTS

| | | | | |
|---|---|---|---|---|
| 3,818,911 | A * | 6/1974 | Fournier | A61F 13/38 604/1 |
| 4,772,274 | A | 9/1988 | Lukacs | |
| 5,778,475 | A * | 7/1998 | Garcia | A46B 15/0055 15/111 |
| 6,379,341 | B1 | 4/2002 | Cho | |
| 7,112,184 | B2 | 9/2006 | Bichsel et al. | |
| 7,211,061 | B1 * | 5/2007 | Maxwell | A61M 31/00 604/1 |
| 8,414,551 | B2 * | 4/2013 | Siniawski | A47K 7/00 604/317 |
| 2005/0187507 | A1 | 8/2005 | Reed et al. | |
| 2011/0264060 | A1 | 10/2011 | Siniawski et al. | |

OTHER PUBLICATIONS

Written Opinion of the International Searching Authority dated Oct. 29, 2018 in corresponding International Application No. PCT/US2018/027733 filed Apr. 16, 2018; total 6 pages.

International Preliminary Report on Patentability dated Oct. 29, 2018 in corresponding International Application No. PCT/US2018/027733 filed Apr. 16, 2018; total 7 pages.

* cited by examiner

FEMININE CLEANING DEVICE

CROSS REFERENCE TO RELATED APPLICATIONS

This application claims priority to and the benefit of U.S. Provisional Patent Application No. 62/485,783, titled "Feminine Cleaning Device" and filed on Apr. 14, 2017, the entire contents of which is herein incorporated by reference in its entirety.

BACKGROUND

1. Field

The present disclosure is directed to a feminine cleaning device or brush for adult women for cleaning their vagina.

2. Description of the Related Art

The vagina is an elastic canal with a soft, flexible lining that provides lubrication and sensation. The vagina connects the uterus to the outside of the body. The vulva and labia form the entrance of the vagina, and the cervix of the uterus protrudes into the vagina, forming the interior end. The vagina receives the penis during sexual intercourse and also serves as a conduit for menstrual flow from the uterus. During childbirth, the baby passes through the vagina, which is sometimes referred to as the birth canal.

Bacteria, discharge, menstrual flow, semen, and other impurities can attach to or reside in the vagina. These impurities can cause inflammation of the vagina and can result in yeast infections or bacterial overgrowth. These impurities can also cause adult woman to experience discomfort, itching, pain and bad odor in the vagina.

Some products and methods have been used to clean the vagina. For example, a douche can be used to spray water or other mixtures into the vagina to clean the vagina. This method is often referred to as douching. Some adult women use warm water and a mild soap to clean the vagina; however, some adult women are too sensitive to soap or hypoallergenic products and do not prefer to use these products.

Furthermore, these products and methods have additional drawbacks and shortcomings. For example, they are unable to remove some impurities that may be attached or stuck to the walls of the vagina or they may not be able to effectively clean the vagina. Accordingly, new products and methods are needed to safely and effectively clean the vagina and prevent impurities and unhealthy bacteria from attaching to the walls of the vagina or residing in the vagina.

Therefore, there is a need for better products for adult women to clean their vagina.

SUMMARY

The present disclosure is directed to a feminine cleaning device or brush for adult women for cleaning their vagina. The feminine cleaning brush includes a handle, a cleaning portion having rings arranged substantially parallel to one another and a groove positioned between adjacent rings. The number of rings being at least 10 and preferably between 10 and 30 and the number of grooves being at least 10 and preferably between 10 and 30. The feminine cleaning brush includes a middle portion positioned between the handle and the cleaning portion and a tapered tip extending from the cleaning portion. The tapered tip is provided for an easier and smoother insertion into the vagina.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Figure 1:
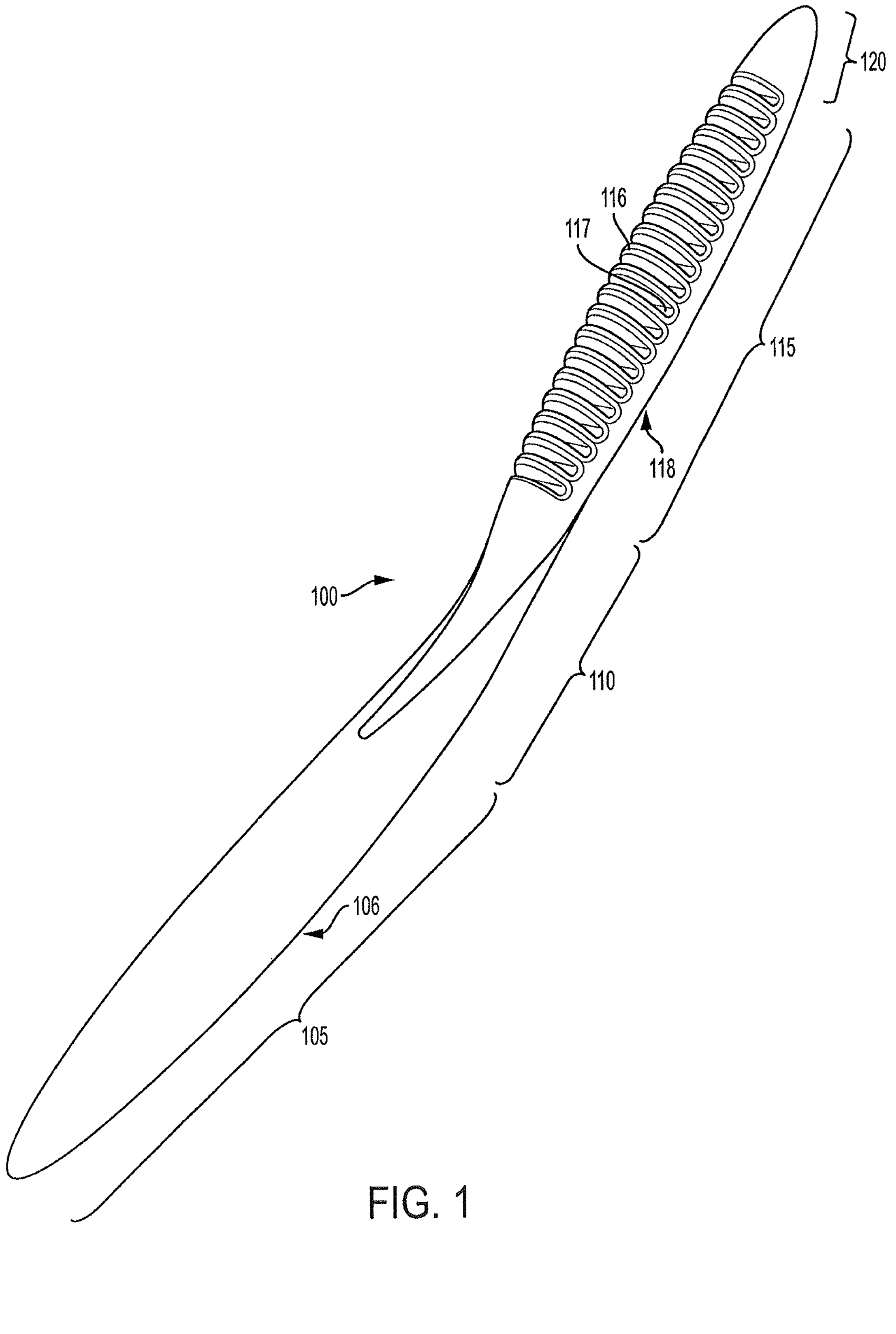
FIG. 1 is a front perspective view of a feminine cleaning brush according to an embodiment of the present disclosure.
Figure 2:
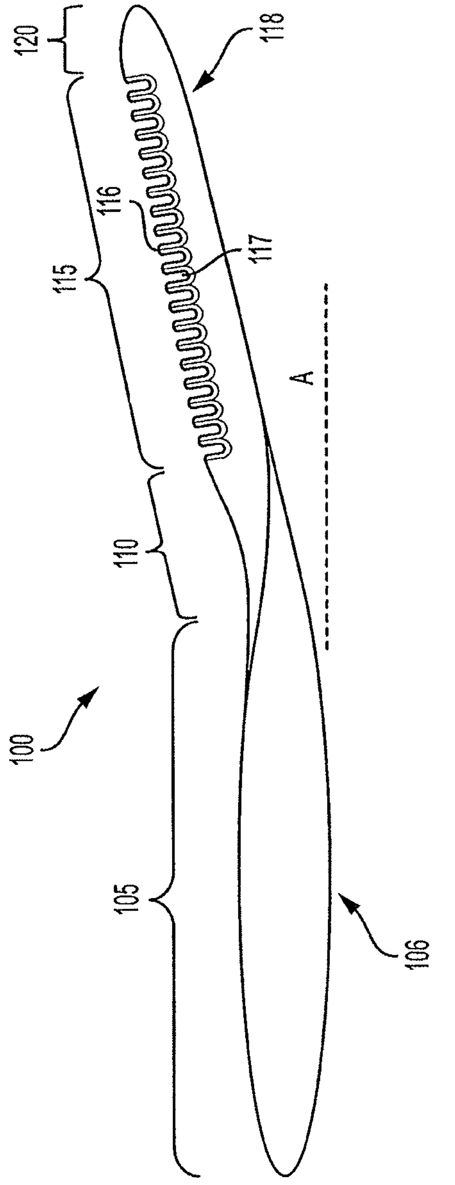
FIG. 2 is a right side view of the feminine cleaning brush of FIG. 1 according to an embodiment of the present disclosure.
Figure 3:
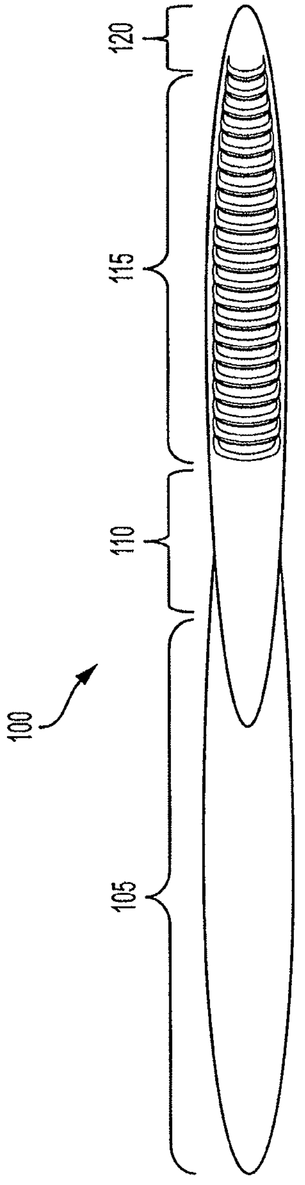
FIG. 3 is a front view of the feminine cleaning brush of FIG. 1 according to an embodiment of the present disclosure.
Figure 4:
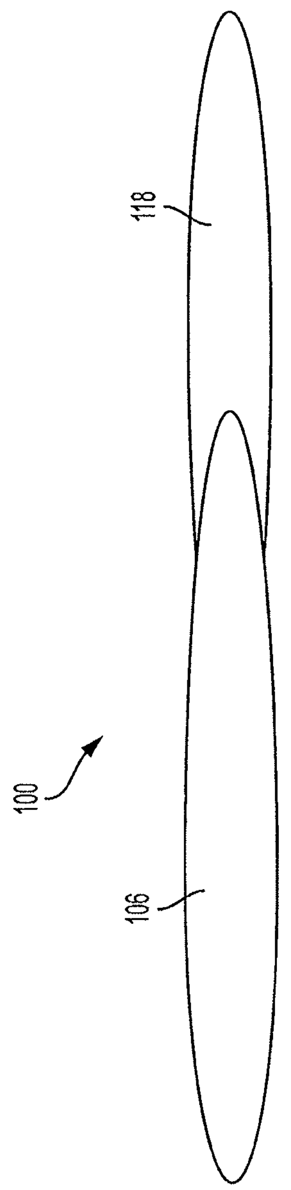
FIG. 4 is a rear view of the feminine cleaning brush of FIG. 1 according to an embodiment of the present disclosure.

FIG. 1 is a front perspective view of a feminine cleaning brush 100 (also can be referred to as a feminine cleaning device 100). FIG. 2 is a right side view, FIG. 3 is a front view, and FIG. 4 is a rear view of the feminine cleaning brush 100 of FIG. 1. Referring to FIGS. 1-4, the brush 100 is used by adult women for cleaning their vagina. The brush 100 is great for women who are sensitive to soap or hypoallergenic products. The brush 100 is generally not used with crémes, lotions, oils, medicines or soaps. The brush 100 effectively cleans the inside of the vagina for when women are on or off their menstrual cycle. The brush 100 is effective at removing bacterial and reduces the likelihood of infections within the vagina. The brush 100 can be easily cleaned using soap and warm water.

The brush 100 has a handle 105, a flexible middle portion 110, a cleaning portion 115, and a tapered tip 120. The handle 105 can have a rear flat portion 106 or a rear rounded portion 106. For example, the handle 105 can have a rear flat portion 106 that can be used to rest the brush 100 on a flat surface (e.g., a counter or a shower ledge) such that the cleaning portion 115 is elevated to avoid contact or contamination with the flat surface. The handle 105 can have a length of between about 7.62 centimeters (cm) (3 inches) and 10.16 cm (4 inches) and a diameter of about 1 cm. The length is sized to allow the adult woman to have a good grip of the brush 100 for cleaning the vagina. In one embodiment, the handle 105 has a thicker diameter center and is tapered or sloped towards both ends and has a rounded bottom end. The top end of the handle 105 is attached or connected to the flexible middle portion 110. The handle 105 is made of a soft rubber material or a plastic material that is easy to grip, hold and control the movement of the brush 100.

The flexible middle portion 110 is tapered and curved and smaller in diameter than a center portion of the handle 105 to allow for some flexibility and bendability of the brush 100. Alternatively, the middle portion 110 is relatively rigid and only bends slightly. As shown in FIG. 2, the curved angle A is between 10 degrees and 30 degrees, for example, and allows for easier use and better and more effective insertion into and cleaning of the vagina. The tapered flexible middle portion 110 can also be used for placement of the user's thumb or finger for better grip, control and movement of the brush 100. The flexible middle portion 110 can have a length of about 2.54 cm (1 inch) and a tapered shape with a center diameter of less than 1 cm.

As the adult woman holds the handle 105, the tapered tip 120 can be slowly and softly inserted into the vagina. The tapered tip 120 is smooth, soft and curved such that its end is smaller and thinner than its base for, an easier and smoother insertion into the vagina. In one embodiment, the tapered tip 120 is formed in the shape of a cone with a smooth, rounded end tip.

The cleaning portion 115 can lie along a straight axis or can be further curved in the same direction and with the same or similar radius of curvature as the flexible middle portion 110. For example, the cleaning portion 115 can be slightly curved (e.g., having a large radius of curvature) so that the brush 100 is slightly and smoothly curved from the flexible middle portion 110 to the tapered tip 120. The curve of the cleaning portion 115 can be between 10 degrees and 30 degrees to allow for easier use and better and more effective insertion into and cleaning of the vagina. The curve of the flexible middle portion 110 and/or the cleaning portion 115 advantageously provides a better coincident angle or curve between the cleaning portion 115 and the vagina walls for a more comfortable and effective cleaning of the vagina. That is, substantially all or most of the cleaning portion 115 is able to rub or smoothly glide across a large portion or surface of the vaginal walls for a better and more thorough cleaning of the vagina.

The cleaning portion 115 advantageously have soft, smooth rubber rings 116 that scrape or clean the inside of the vagina and grooves 117 that capture the bacteria and clean the vagina as the user slowly and softly moves the cleaning portion 115 inside the vagina or along the vaginal walls. That is, the rings 116 move or direct the impurities into the grooves 117, which hold or capture the impurities. The adult woman generally holds the handle 105 and slowly inserts the tapered tip 120 followed by the cleaning portion 115 into the vagina. Then, the adult woman slowly moves the brush 100 with a circular movement inside the vagina so that the cleaning portion 115 moves within the vagina and/or comes into contact with the vaginal walls and any impurities are dislodged or moved by the rubber soft, smooth rings 116 and scooped up or captured by the grooves 117.

The rings 116 can also be referred to as curved, smooth and/or rounded circular protrusions 116. The rings 116 are arranged substantially parallel to one another with a groove 117 positioned between adjacent rings 116. The grooves 117 can also be referred to as channels 117 that are used to hold or retain bacteria or other vaginal fluid or material. The grooves 117 may be coated with a sticky adhesive material to better hold or retain bacteria or other vaginal fluid or material.

In some embodiments, the rings 116 and the grooves 117 are alternating and can range in number from 10-30 each. The number of rings can be at least 10 and preferably between 10 and 30 and the number of grooves can be at least 10 and preferably between 10 and 30. The rings 116 can be semi-circular (as shown) or complete circles and travel around the entire cleaning portion 115. The semi-circular configuration of the rings 116 allows for the rear portion 106 and side portion 118 of the cleaning portion 115 to be smooth to allow for easier and smoother insertion, removal and cleaning of the vagina. The rings 116 are rounded, smooth and tapered and are generally positioned parallel to one another with a groove 117 in between adjacent rings 116. The rings 116 are smooth and can bend or flex to allow for a softer and gentler insertion, cleaning, and removal of the cleaning portion 115 into and out of the vagina. In some embodiments, the rings 116 can be arranged at an angle or in a criss-crossed configuration.

The cleaning portion 115 has a length of between about 6.35 cm (2.5 inches) and 8.89 cm (3.5 inches) and a diameter of about 1 cm. The rings 116 can be about 0.2 cm to 0.25 cm apart and the grooves 117 can be about 0.2 cm to 0.25 cm wide and about 0.2 cm to 0.6 cm deep.

The brush 100 can be made of a soft rubber material and/or & plastic material with smooth corners throughout. For example, the inner portion of the brush 100 can be made of a plastic material and the outer portion of the brush 100 can be made of a soft rubber material and the two materials are co-molded together to form a single uni-body device. The inner plastic portion can provide a relatively stronger (less bendable) core and the outer rubber portion can be softer and smoother for contact with and cleaning of the vagina. The inner portion and/or the outer portion can also be made of a silicon material. In various embodiments, the brush 100 can be made entirely of a plastic material or a rubber material. That is, the brush 100 can be a single uni-body device where the entire device is a single part and made of the same material or multiple materials. The single uni-body device can be disposable after one or more uses depending on the circumstances.

Figure 5:
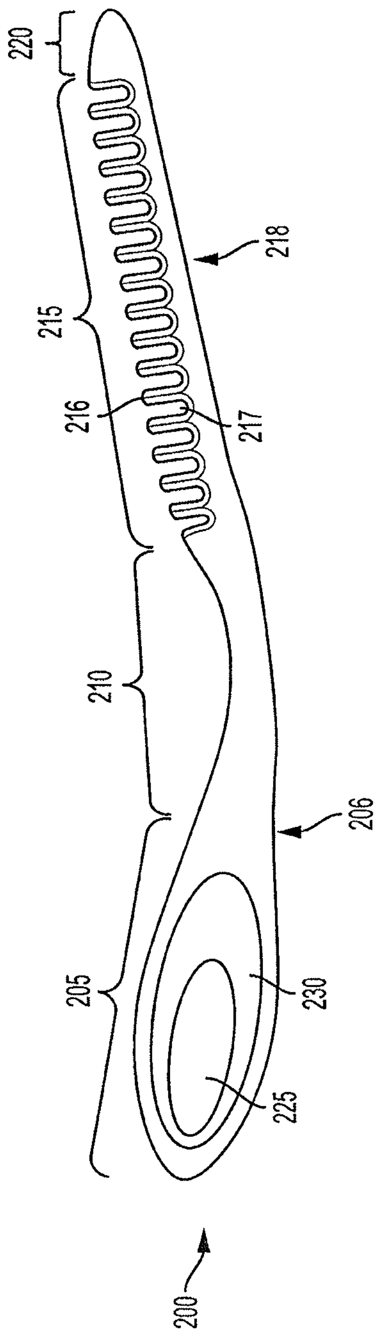
FIG. 5 is a right side view of a feminine cleaning brush according to an embodiment of the present disclosure.
Figure 6:
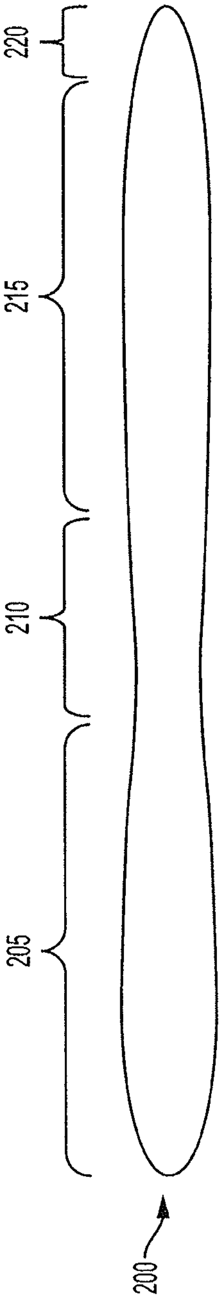
FIG. 6 is a rear view of the feminine cleaning brush of FIG. 5 according to an embodiment of the present disclosure.

FIG. 5 is a right side view of a feminine cleaning brush 200 with an opening or a hole 225 so the brush 200 can be hung on a hook in the shower. As shown, the handle 205 can be much bigger for a better grip. A rubber material 230 can surround the opening 225 to allow the adult woman to have a better grip of the handle 205. The remaining features of brush 200 are similar to brush 100. FIG. 6 is a rear view of the brush 200.

Figure 7:
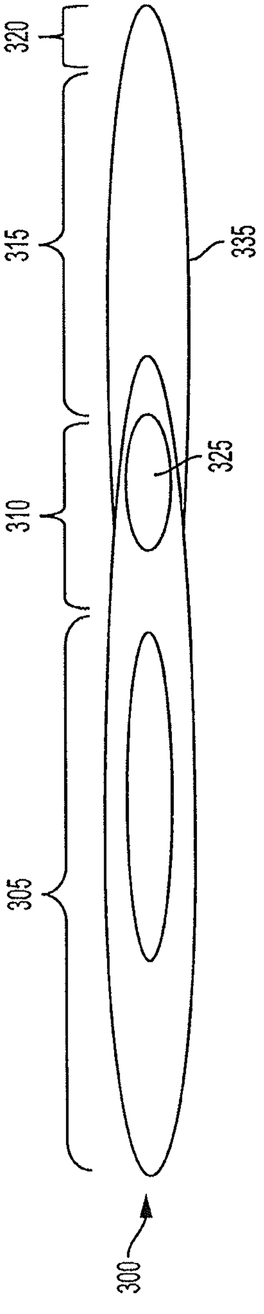
FIG. 7 is a rear view of a feminine cleaning brush according to an embodiment of the present disclosure.

FIG. 7 is a rear view of a feminine cleaning brush 300 with a button or a toggle device 325 that is used to disconnect the cleaning portion 315 from the handle 305 and/or the flexible middle portion 310. That is, when the button 325 is pushed, the cleaning device 315 may be pulled to the right to detach it from the flexible middle portion 310.

Hence, the brush 300 can have multiple parts. For example, the brush 300 can be made of two parts such that the handle 305 and the flexible middle portion 310 can be a first part and the cleaning portion 315 and the tapered tip 320 can be a second part. The second part (e.g., the cleaning portion 315) can be removably fastened or screwed into the first part (e.g., the handle 305) to allow for the cleaning portion 315 to be removed and replaced with a new cleaning portion 315 while the handle 305 is kept for repeated uses.

Figure 8:
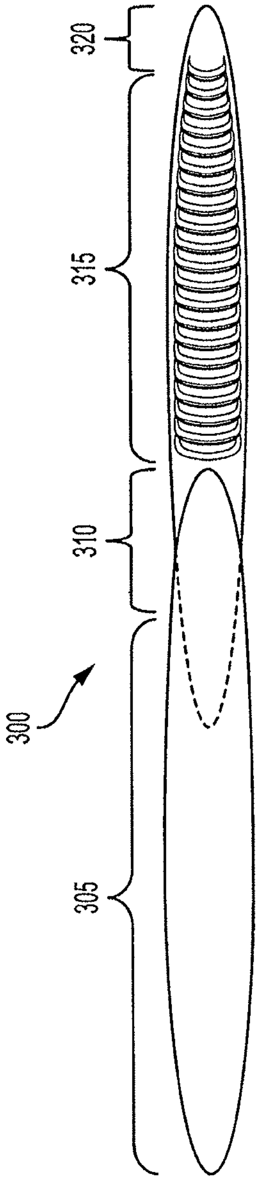
FIG. 8 is a front view of the feminine cleaning brush of FIG. 7 according to an embodiment of the present disclosure.
Figure 9:
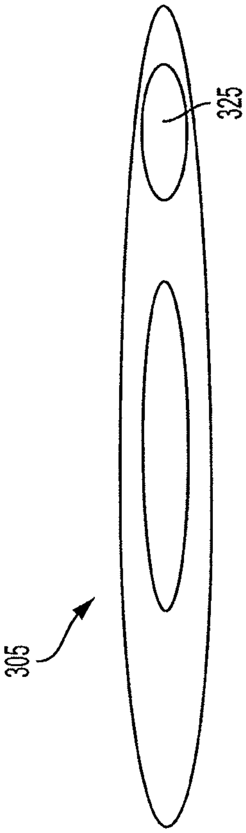
FIG. 9 is a rear view of the handle of the feminine cleaning brush of FIG. 7 according to an embodiment of the present disclosure.
Figure 10:
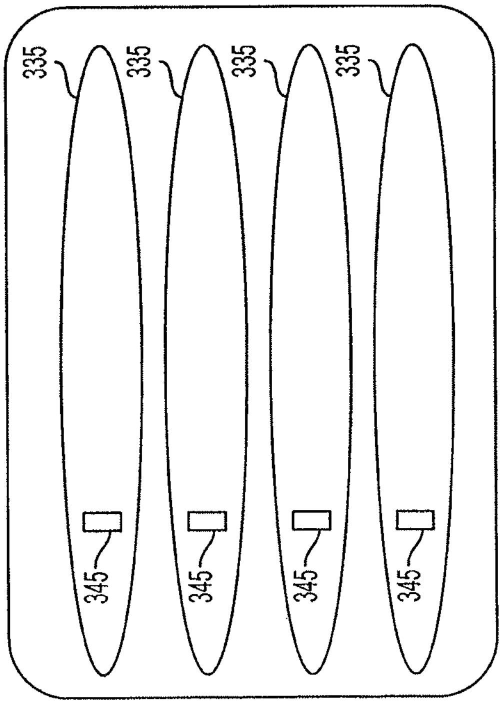
FIG. 10 shows a number of disposable cleaning portions that are removably attachable to the handle shown in FIG. 9 according to an embodiment of the present disclosure.

FIG. 8 is a front view of the brush 300 of FIG. 7. FIG. 9 is a rear view of the handle 305 of the brush 300 of FIG. 7. FIG. 10 shows a number of disposable cleaning portions 335 that are removably attachable to the handle 305 shown in FIG. 9. The disposable cleaning portions 335 may each have a cutout 345 to allow for securing and attachment to the handle 305.

Figure 11:
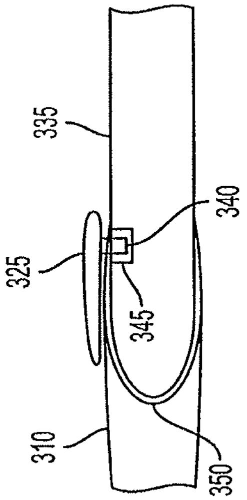
FIG. 11 shows an exploded view of an attachment device used to removably attach the disposable cleaning portions as shown in FIG. 10 to the handle as shown in FIG. 9 according to an embodiment of the present disclosure.

FIG. 11 shows an exploded view of an attachment device used to removably attach the disposable cleaning portions 335 shown in FIG. 10 to the handle 305 shown in FIG. 9. A disposable cleaning portion 335 is inserted into a cavity 350 of the handle 305 or the flexible middle portion 310. That is, one end of the disposable cleaning portion 335 fits snugly into the cavity 350 of the handle 305 or the flexible middle portion 310 so the two parts are tightly secured together. When the disposable cleaning portion 335 is properly and snugly fit into the cavity 350, a hard plastic pin 340 moves into the cutout 345 to lock the disposable cleaning portion 335 in place. The hard plastic pin 340 is connected to the button 325 (or the toggle device 325). The button 325 is connected to the handle 305 or the flexible middle portion 310 and moves or toggles to allow the hard plastic pin 340 to move into and out of the cutout 345. The button 325 and the hard plastic pin 340 move together. When the button 325 is not pushed, the hard plastic pin 340 fit into the cutout 345 and secures the handle 305 or the flexible middle portion 310 to the disposable cleaning portion 335.

When the button 325 is pushed, the hard plastic pin 340 exits the cutout 345 to allow the cleaning portion 315 to be unlocked and detached from the handle 305 or the flexible middle portion 310. The button 325 needs to be continually pushed down to release and detach the disposable cleaning portion 335 from the handle 305 or the flexible middle portion 310. As the button 325 is pushed down, the disposable cleaning portion 335 can be pulled out of the cavity 350 and disposed of. A new disposable cleaning portion 335 can then be inserted into the cavity 350. The remaining features of brush 300 are similar to brush 100.

Figure 12:
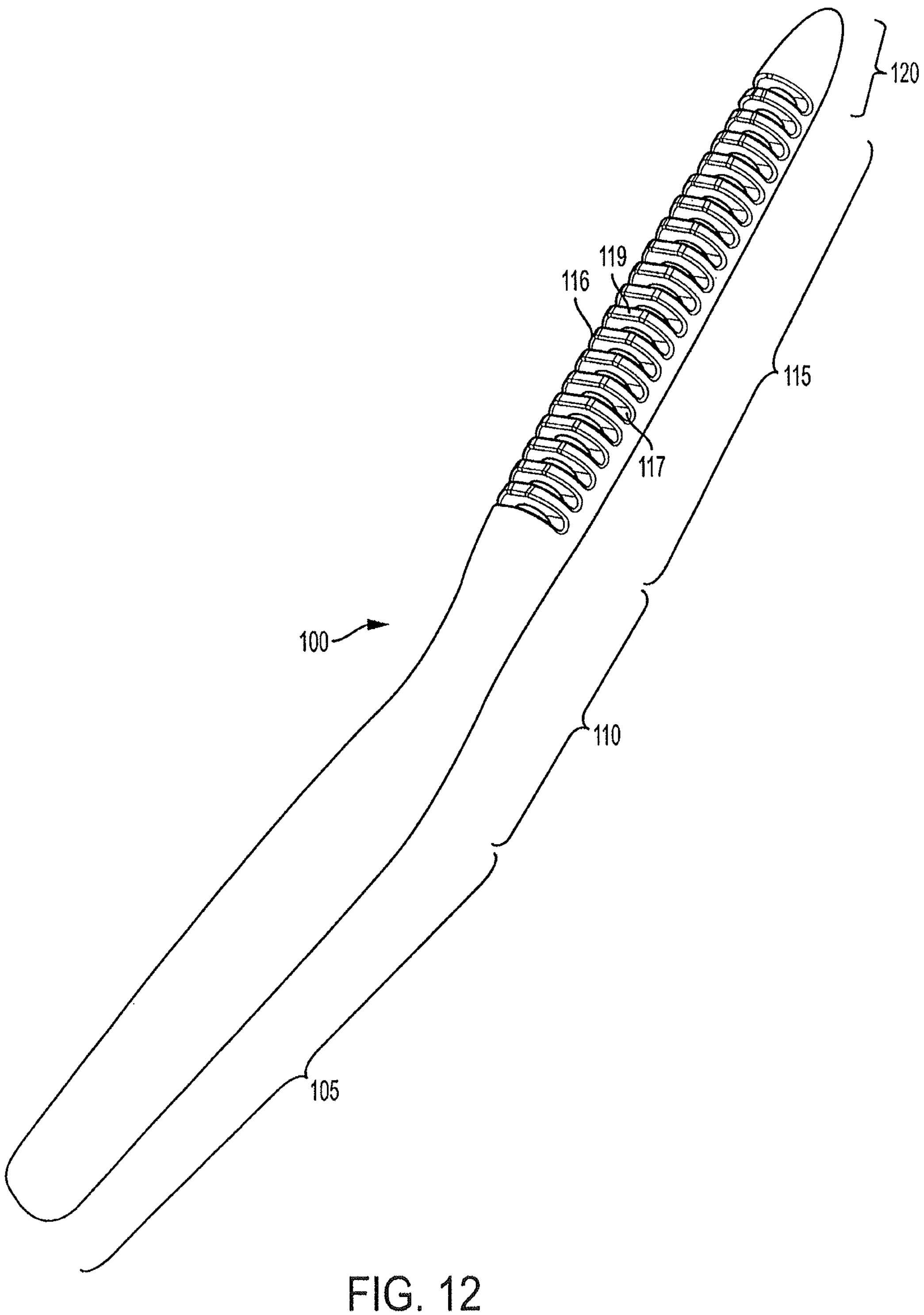
FIG. 12 shows a front perspective view of a feminine cleaning brush according to an embodiment of the present disclosure.

FIG. 12 shows a front perspective view of a feminine cleaning brush 400. As shown, each of the rings 116 has a flat top portion 119. The flat top portion 119 has smooth rounded ends. The flat top portion 119 advantageously allows for a greater surface area to contact the vagina. In one embodiment, the surface area can vary from ring to ring. For example, as shown, the flat top portion 119 for the rings 116 on the ends has a lesser surface area than the flat top portion 119 of the rings 116 in the middle. The remaining features of brush 400 are similar to brush 100.

The foregoing description of the disclosed example embodiments is provided to enable any person of ordinary skill in the art to make or use the present invention. Various modifications to these examples will be readily apparent to those of ordinary skill in the art, and the principles disclosed herein may be applied to other examples without departing from the spirit or scope of the present invention. The described embodiments are to be considered in all respects only as illustrative and not restrictive and the scope of the invention is, therefore, indicated by the following claims rather than by the foregoing description. All changes which come within the meaning and range of equivalency of the claims are to be embraced within their scope.

What is claimed is:

1. A feminine cleaning brush, comprising:
- a handle;
- a cleaning portion having rear and side portions that are continually smooth and a top portion with semi-circular rings that are arranged substantially parallel to one another and a groove positioned between adjacent rings, the number of rings being at least 10 and the number of grooves being at least 10;
- a middle portion positioned between the handle and the cleaning portion; and
- a tapered tip extending from the cleaning portion, the tapered tip formed in the shape of a cone with a smooth, rounded end tip.

2. The feminine cleaning brush of claim 1, wherein the handle has a first diameter and the middle portion has a second diameter that is smaller than the first diameter.

3. The feminine cleaning brush of claim 1, wherein the handle has a rear flat portion.

4. The feminine cleaning brush of claim 1, wherein the middle portion is curved at an angle of between 10 degrees and 30 degrees relative to a horizontal axis.

5. The feminine cleaning brush of claim 1, wherein the cleaning portion is curved at an angle of between 10 degrees and 30 degrees relative to a horizontal axis.

6. The feminine cleaning brush of claim 1, wherein the cleaning portion is curved in the same direction and with the same or similar radius of curvature as the middle portion.

7. The feminine cleaning brush of claim 1, wherein each ring is smooth and rounded.

8. The feminine cleaning brush of claim 1, wherein the rings bend or flex to allow for a softer and gentler cleaning of a vagina.

9. The feminine cleaning brush of claim 1, wherein the rings are arranged at an angle relative to a vertical plane or in a criss-cross configuration.

10. The feminine cleaning brush of claim 1, wherein the grooves form channels for holding or retaining bacteria or other vaginal fluid or material.

11. The feminine cleaning brush of claim 1, wherein the grooves are coated with a sticky adhesive material.

12. The feminine cleaning brush of claim 1, wherein the rings are about 0.2 cm to 0.25 cm apart and the grooves are about 0.2 cm to 0.25 cm wide and about 0.2 cm to 0.6 cm deep.

13. The feminine cleaning brush of claim 1, wherein the handle, the middle portion, the cleaning portion, and the tapered tip is a single uni-body device where the device is a single part and made of a soft rubber or plastic material.

14. The feminine cleaning brush of claim 1, wherein the cleaning portion is removably attached to the middle portion.

15. The feminine cleaning brush of claim 1, wherein the number of rings is between 10 and 30 and the number of grooves is between 10 and 30.

16. The feminine cleaning brush of claim 1, wherein each of the rings has a flat top portion.

17. The feminine cleaning brush of claim 16, wherein the flat top portion for the rings on the ends has a lesser surface area than the flat top portion of the rings in the middle.

* * * * *